(12) United States Patent
Lundgren

(10) Patent No.: US 6,468,225 B1
(45) Date of Patent: *Oct. 22, 2002

(54) METHOD AND APPARATUS FOR COLLECTING BONE TISSUE FRAGMENTS

(75) Inventor: Dan Lundgren, Howas (SE)

(73) Assignee: Astra Tech AB, Molndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,758

(22) Filed: May 26, 2000

Related U.S. Application Data

(63) Continuation of application No. 08/819,403, filed on Mar. 17, 1997, now Pat. No. 6,083,175, which is a continuation of application No. PCT/SE95/01065, filed on Sep. 20, 1995.

(30) Foreign Application Priority Data

Sep. 20, 1994 (SE) .............................................. 9403183

(51) Int. Cl.$^7$ .............................................. A61B 10/00
(52) U.S. Cl. ..................... 600/562; 600/573; 433/90
(58) Field of Search .................................. 600/562, 563, 600/573; 433/89, 90, 91, 92, 215

(56) References Cited

U.S. PATENT DOCUMENTS

| 3,623,607 | A |   | 11/1971 | Loos ........................... 210/106 |
|---|---|---|---|---|
| 3,785,380 | A |   | 1/1974 | Brumfield ..................... 604/119 |
| 3,863,624 | A |   | 2/1975 | Gram .......................... 128/2 B |
| 3,890,712 | A |   | 6/1975 | Lopez ........................... 433/92 |
| 4,018,686 | A |   | 4/1977 | Shufflebarger et al. ..... 210/448 |
| 4,083,706 | A |   | 4/1978 | Wiley ......................... 55/385.1 |
| 4,468,217 | A |   | 8/1984 | Kuzmick et al. ............. 604/48 |
| 4,886,492 | A |   | 12/1989 | Brooke ........................ 604/541 |
| 5,114,240 | A |   | 5/1992 | Kindt-Larsen et al. ...... 366/129 |
| 5,192,439 | A |   | 3/1993 | Roth et al. ................... 210/485 |
| 5,494,044 | A |   | 2/1996 | Sundberg ..................... 600/562 |
| 5,830,359 | A |   | 11/1998 | Knight et al. ................ 210/651 |
| 6,083,175 | A | * | 7/2000 | Lundgren ..................... 600/562 |

FOREIGN PATENT DOCUMENTS

| EP | 0 284 322 | 9/1988 |
|---|---|---|
| JP | 5-137736 | 6/1996 |

* cited by examiner

Primary Examiner—Kevin Shaver
Assistant Examiner—Charles Marmor, II
(74) Attorney, Agent, or Firm—Merchant & Gould P.C.

(57) ABSTRACT

Bone tissue fragments are collected from liquid fluid being evacuated by suction from a surgical operation in bone tissue. Liquid is allowed to pass into the cylindrical sieve through one open end thereof and through the sieve wall from the inside to the outside thereof. Bone tissue fragments are collected on the inside surface of the sieve and are scraped off and deposited outside the sieve.

28 Claims, 1 Drawing Sheet

METHOD AND APPARATUS FOR COLLECTING BONE TISSUE FRAGMENTS

This application is a continuation of U.S. Ser. No. 08/819,403 filed Mar. 17, 1997 now U.S. Pat. No. 6,083,175, which is a continuation of PCT/SE95/01065 filed on Sep. 20, 1995.

FIELD OF THE INVENTION

The invention relates to an apparatus for collecting bone tissue fragments from liquids recovered during surgical operations, as well as to a method of collecting bone tissue fragments.

BACKGROUND OF THE INVENTION

Many surgical operations are carried out in bone tissue. An example includes those operations conducted within the oral cavity for the purpose of fixing dental problems such as crowns, bridges and prosthesis in toothless regions of the jaw. These operations can include drilling holes in the jaw bone to secure titanium screws that are used as anchoring elements. The bone tissue fragments generated during drilling can be used for filling bone cavities within the jaw that were caused by proceeding pathological processes.

An aspirator can be used to remove blood from the operative site. The bone tissue fragments created during the operation (such as drilling) are entrained within the liquid flow and will be lost if they are not separated from the liquid flow and collected. Accordingly, a need remains for a simple way for collecting bone tissue fragments.

SUMMARY OF THE INVENTION

Accordingly, the invention is found in a method for collecting bone tissue fragments from liquid evacuated during a surgical operation within bone tissue. The liquid evacuated by suction is passed into a cylindrical sieve through an open end. The liquid passes through the sieve wall from an inside surface to an outside surface. An end wall which is displaceably disposed it the opposite end of the sieve is then moved axially through the cylindrical sieve so that bone tissue fragments collected on the inside surface of the sieve are scraped off from the inner surface and are deposited outside the sieve from the open end of the sieve.

The invention is also found in a device for collecting bone tissue fragments during surgical operations within bone tissue. The device is cylindrical, with an inlet at one end and an outlet at the other end. The cylindrical device is connected to a suction conduit and there is a cylindrical sieve provided within the device. A space is provided between the outer curved surface of the sieve and the inner curved surface of the cylinder. An open end of the sieve communicates with the inlet of the cylinder and the space communicates with the outlet of the cylinder. The other end of the sieve has an end wall that can be displaced axially through the sieve as a piston.

DETAILED DESCRIPTION

Figure 1:
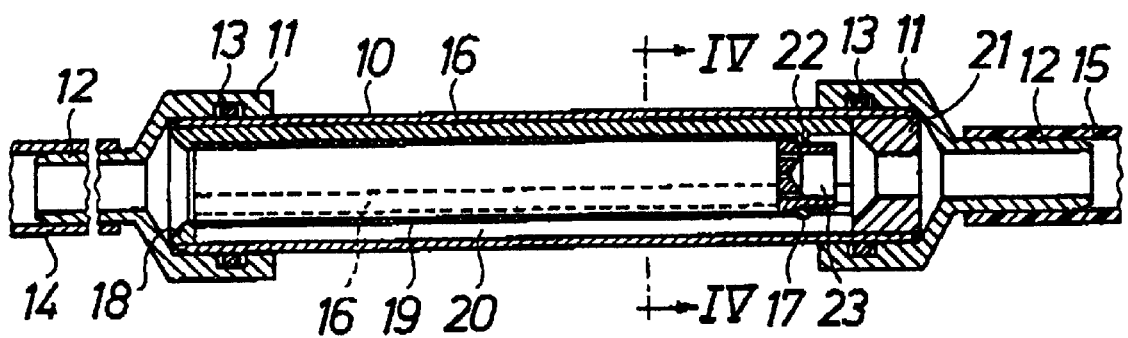
FIG. 1 is an axial cross-sectional view of a device for evacuating liquid by suction and removing bone fragments from the liquid according to the invention.

The device according to the invention comprises a cylinder 10 open at each end.

A cover 11 is pushed onto the cylinder 10 at each open end, forming a connection piece 12 and being sealed against the outside surface of the cylinder 10 with an O-ring 13. An aspirator nozzle 14 (seen in fragmentary detail only) is connected to one of the connection pieces (being the left one in FIG. 1). A suction hose 15 is connected to the other connection piece (the right side in FIG. 1) and is also connected to an aspirator (not shown). The left connection piece and aspirator nozzle 14 form an inlet of the cylinder 10 while the right connection piece and suction hose 15 form an outlet of the cylinder 10.

Figure 4:
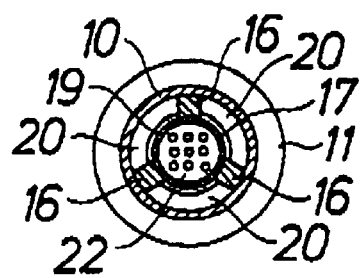
FIG. 4 is a cross-sectional view along line 4—4 of FIG. 1.

A cage comprising three straight bars 16 that extend in parallel and are equally spaced circumferentially and two rings 17 and 18 that are integral with and interconnect the straight bars, fits detachably in the cylinder 10. The cage receives a cylindrical sieve 19. The cage serves to keep the outside curved surface of the sieve 19 spaced apart from the inside curved surface of the cylinder 10. As a result, the axially extending spaces 20 (as seen in FIG. 4) are maintained. These spaces 20 are separated from the inlet of the cylinder 10 via ring 18, but communicate with the outlet of the cylinder 10 through an annular plug 21 that is fixed in the cylinder 10.

At the end of the sieve adjacent the outlet of the cylinder 10, an end wall 22 is provided that has a thicker portion that fits against the inside surface of the sieve 19 and a narrower portion that forms a hollow stud 23 that fits displaceably in ring 17 when the wall is in the end position as shown in FIG. 1. End wall 22 is axially displaceable along the inside surface of the sieve 19. In the embodiment shown, the end wall 22 is perforated. If the end wall 22 is perforated, it is preferable that the apertures within end wall 22 be smaller than the apertures of sieve 19. Perforations in end wall 22 are not necessary, however. Preferably, the device shown in FIG. 1 is made entirely of plastic and is disposable.

During use. the device is preferably connected in a suction conduit between the aspirator nozzle 14 and the suction hose 15. Low pressure or vacuum is maintained within the suction conduit. If used while drilling occurs in the jaw bone, rinse fluid and blood will be sucked into the sieve 19 via the inlet of the cylinder 10 and will pass through the wall of the sieve 19 into spaces 20 and will then continue to the outlet. Some flow will pass directly to the outlet through perforated end wall 22. The low pressure or vacuum will hold the end wall in the position seen in the Figures as the thicker portion can not pass through ring 17. If the liquid contains coagulated blood or bone tissue fragments, the perforations within end wall 22 will quickly become clogged and the solid particles within the liquid will accumulate on the inside surface of the sieve 19 However, the perforations within end wall 22 provide for a direct continuous flow as long as there are no solid particles to recover.

Figure 2:
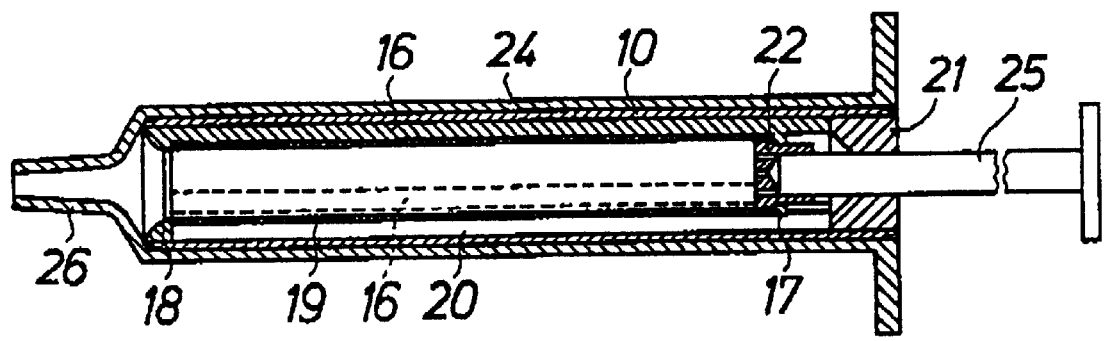
FIG. 2 is a view of the device of FIG. 1, shown in use.
Figure 3:
FIG. 3 is an end view of the axially displaceable end wall in the sieve.

In order to recover the material collected in the sieve 19, cylinder 10 is disconnected from end pieces or hoods 11 and is placed within the cylinder 24 of an ordinary syringe as seen in FIG. 2. A piston rod 25 is then connected to the end wall 22 by inserting the piston rod 25 into stud 23. The end wall 22 is then displaced by moving the piston rod 25 axially through the cylindrical sieve 19, thereby scraping the collected material off from the inside surface of the sieve wall. The material is deposited through connection piece 26 of the cylinder, where the connection piece 26 can be constructed as a Luer connection for connecting a suitable mouth piece to the syringe cylinder.

However, it is not necessary to move cylinder 10 to a syringe for deposition. Instead, it is possible to connect the piston rod to the end wall through the right connection piece 12 (as seen in FIG. 1) and to deposit the material through the left connection piece 12 (of FIG. 1). It may be easier or more comfortable, however, to use a syringe for deposition.

What is claimed is:

1. A method for collecting bone tissue fragments from a liquid fluid flow at a surgical operation in bone tissue, the method comprising the steps of:

evacuating liquid fluid by suction from a surgical site;

passing the evacuated liquid fluid into a tube at a first open end thereof and through a sieve located in the tube through a first open end of the sieve and through a wall of the sieve from an inner surface to an outer surface, wherein the bone tissue fragments are trapped on the inner surface of the sieve;

draining the liquid fluid from the tube at a second open end thereof;

inserting a piston rod through said second open end of the tube and a second open end of the sieve to engage a piston therein;

manually displacing the piston rod axially through the sieve to scrape bone tissue fragments from the inner surface of the sieve with the piston; and depositing the scraped off bone tissue fragments outside the sieve through the first open end of the sieve and the first open end of the tube.

2. A method as claimed in claim 1, wherein said sieve is cylindrical.

3. A device for collecting bone tissue fragments from a liquid flow at a surgical operation in bone tissue, the device comprising;

a tube having axially aligned inlet and outlet sockets at either end of the tube for connection into a suction conduit;

a sieve disposed in the tube, so as to define a space between an outer surface of the sieve and an inner surface of the tube, wherein the space is in communication with the outlet socket of the tube;

a piston displaceably disposed within the sieve, the piston engaging an inner surface of the sieve, wherein the piston forms an end wall in the sieve at an outlet socket end of the sieve; and a piston rod insertable into the tube through the outlet socket to engage the piston for manual axial displacement through the sieve for deposition of the bone fragments, trapped by the sieve, through the inlet socket of the tube.

4. A device as claimed in claim 3, wherein said sieve is cylindrical.

5. A device as claimed in claim 4, wherein said sieve is cylindrical.

6. A device for collecting bone tissue fragments from a liquid fluid flow at a surgical operation in bone tissue, the device comprising:

a tube having a tube inlet and a tube outlet for connection into a suction conduit;

a tubular sieve arranged in the tube between the tube inlet and the tube outlet and adapted to collect bone tissue fragments on an inner sieve surface;

a cage fitting in which the sieve is mounted, the cage fitting comprising spacers between the sieve and the tube for providing a space between the sieve and the tube in communication with the tube outlet; and an end wall displaceably arranged in the sieve.

7. A device as claimed in claim 6, wherein said spacers comprises axially extending bars.

8. A device as claimed in claim 7, wherein said cage fitting further presents first and second rings interconnecting said axially extending bars.

9. A device as claimed in claim 8, wherein said first ring is arranged at an end of the sieve adjacent the tube inlet and is in engagement with both the tube and the sieve in order to prevent liquid fluid to flow directly from the tube inlet into said space without first passing through the sieve.

10. A device as claimed in claim 6, wherein the cage fitting with the sieve mounted therein is detachably fitted in the tube.

11. A device as claimed in claim 10, further comprising a piston rod insertable into the tube through the tube outlet to engage the end wall for manual axial displacement of the end wall through the sieve.

12. A device as claimed in claim 6, wherein said end wall comprises a piston displaceably disposed within the sieve and engaging said inner sieve surface for deposition of the bone fragments collected on said inner sieve surface through the tube inlet.

13. A device as claimed in claim 6, wherein said cage fitting is so constructed that, when supporting the sieve in the tube, the cage fitting does not restrict the liquid flow having passed through the sieve.

14. A device as claimed in claim 6, wherein at least a portion of the sieve proximate the tube outlet is supported by said cage fitting at only an outer surface of the sieve.

15. A device as claimed in claim 6, wherein said sieve is cylindrical.

16. A device as claimed in claim 6, wherein said end wall is arranged in the sieve at a distance from the tube inlet.

17. A device as claimed in claim 16, wherein said end wall is arranged in the sieve adjacent the tube outlet.

18. A device for collecting bone tissue fragments from a liquid flow at a surgical operation in bone tissue, the device comprising:

a tube having a tube inlet and a tube outlet for connection into a suction conduit;

a tubular sieve arranged in the tube between the tube inlet and the tube outlet and adapted to collect bone tissue fragments on an inner sieve surface;

a cage fitting in which the sieve is mounted, the cage fitting comprising spacers between the sieve and the tube for providing a space between the sieve and the tube in communication with the tube outlet; and an end wall arranged in the sieve, wherein at least a portion of the sieve proximate the tube outlet is supported by said cage fitting at only an outer surface of the sieve.

19. A device as claimed in claim 18, wherein said spacers comprises axially extending bars.

20. A device as claimed in claim 19, wherein said cage fitting further presents first and second rings interconnecting said axially extending bars.

21. A device as claimed in claim 20, wherein said first ring is arranged at an end of the sieve adjacent the tube inlet and is in engagement with both the tube and the sieve in order to prevent liquid to flow directly from the tube inlet into said space without first passing through the sieve.

22. A device as claimed in claim 18, wherein the cage fitting with the sieve mounted therein is detachably fitted in the tube.

23. A device as claimed in claim 18, wherein said end wall is displaceably arranged in the sieve.

24. A device as claimed in claim 23, wherein said end wall comprises a piston displaceably disposed within the sieve and engaging said inner sieve surface for deposition of the bone fragments collected on said inner sieve surface through the tube inlet.

25. A device as claimed in claim 23, further comprising a piston rod insertable into the tube through the tube outlet to engage the end wall for manual axial displacement of the end wall through the sieve.

26. A device as claimed in claim 18, wherein said cage fitting is so constructed that, when supporting the sieve in the tube, the cage fitting does not restrict the liquid flow having passed through the sieve.

27. A device as claimed in claim 18, wherein said end wall is arranged in the sieve at a distance from the tube inlet.

28. A device as claimed in claim 27, wherein said end wall is arranged in the sieve adjacent the tube outlet.

* * * * *

UNITED STATES PATENT AND TRADEMARK OFFICE
CERTIFICATE OF CORRECTION

PATENT NO.   : 6,468,225 B1
DATED        : October 22, 2002
INVENTOR(S)  : Lundgren It is certified that error appears in the above-identified patent and that said Letters Patent is hereby corrected as shown below:

<u>Column 3,</u>
Line 53, "A device as claimed in claim 4" should read -- A device as claimed in claim 18 --

Signed and Sealed this

Tenth Day of June, 2003

JAMES E. ROGAN
*Director of the United States Patent and Trademark Office*